United States Patent
Andrews et al.

(10) Patent No.: US 12,194,305 B2
(45) Date of Patent: Jan. 14, 2025

(54) ELECTRODE PAD CARTRIDGE FOR DEFIBRILLATORS

(71) Applicant: Avive Solutions, Inc., San Francisco, CA (US)

(72) Inventors: Gordon Mosely P. Andrews, Ross, CA (US); Rory M. Beyer, San Mateo, CA (US)

(73) Assignee: Avive Solutions, Inc., Brisbane, CA (US)

( * ) Notice: Subject to any disclaimer, the term of this patent is extended or adjusted under 35 U.S.C. 154(b) by 405 days.

(21) Appl. No.: 17/725,452

(22) Filed: Apr. 20, 2022

(65) Prior Publication Data

US 2022/0241600 A1 Aug. 4, 2022

Related U.S. Application Data

(63) Continuation-in-part of application No. 16/582,920, filed on Sep. 25, 2019, now Pat. No. 11,331,471.

(60) Provisional application No. 62/810,059, filed on Feb. 25, 2019, provisional application No. 62/737,032, filed on Sep. 26, 2018.

(51) Int. Cl.
*A61N 1/39* (2006.01)

(52) U.S. Cl.
CPC ......... *A61N 1/3968* (2013.01); *A61N 1/3904* (2017.08); *A61N 1/3931* (2013.01)

(58) Field of Classification Search
CPC ... A61N 1/3968; A61N 1/3904; A61N 1/3931
USPC .......................................................... 607/5
See application file for complete search history.

(56) References Cited

U.S. PATENT DOCUMENTS

| | | | |
|---|---|---|---|
| 5,868,790 A | 2/1999 | Vincent et al. | |
| 7,570,994 B2* | 8/2009 | Tamura | H02J 50/05 600/300 |
| 7,715,913 B1 | 5/2010 | Froman et al. | |
| 7,801,605 B2 | 9/2010 | Smirles et al. | |
| 7,822,488 B2 | 10/2010 | Jonsen et al. | |
| 8,185,197 B2 | 5/2012 | Vaisnys et al. | |
| 8,280,506 B2 | 10/2012 | Vaisnys et al. | |
| 8,676,311 B2 | 3/2014 | Cordaro et al. | |
| 8,774,916 B2 | 7/2014 | Vaisnys et al. | |
| 9,511,239 B2 | 12/2016 | Prew et al. | |
| 9,675,810 B2 | 6/2017 | McIntyre et al. | |
| 11,266,826 B2 | 3/2022 | Andrews et al. | |
| 2002/0082644 A1 | 6/2002 | Picardo et al. | |
| 2003/0023274 A1* | 1/2003 | Chesley | A61N 1/3904 607/5 |
| 2010/0228332 A1 | 9/2010 | Hauge et al. | |

(Continued)

OTHER PUBLICATIONS

Philips, "OnSite Defibrillator" Owner's Manual, M5066A, Edition 15, 88 pages, Jun. 2019.

(Continued)

*Primary Examiner* — Nadia A Mahmood
(74) *Attorney, Agent, or Firm* — Beyer Law Group LLP

(57) ABSTRACT

A variety of electrode pad cartridges are described that are suitable for use with a defibrillator. In one aspect the cartridge includes a housing, a tray that carries one or more defibrillation electrode pads and a presence sensor. The presence sensor configured to detect the presence of the tray at a home position. In some embodiments, the AED is configured to be activated when the tray is pulled from the home position.

24 Claims, 10 Drawing Sheets

(56) References Cited

U.S. PATENT DOCUMENTS

2014/0323923 A1 10/2014 Khuon et al.
2017/0131167 A1 5/2017 Doering et al.
2020/0094044 A1 3/2020 Andrews et al.

OTHER PUBLICATIONS

HeartSine "Samaritan Pad 350P/360P AED's, Semi-Automatic/Fully Automatic Public Access Defibrillators" Data Sheet, 4 pages, 2019.
HeartSine "Samaritan Pad 350P/360P AED's, Connected AEDs" Data Sheet, 4 pages, 2019.
Philips, "Cardiac Resuscitation, HeartStart OnSite" brochure, 8 pages, Jun. 2019.
PhysioControl "Lifepak AED Response System" brochure, 12 pages, 2017.
Philips, "HeartStart OnSite Replacement Pads Cartridge", https://www.heartsmart.com/Philips-heartstart-hs1-adult-pad-m5071a-p/M5071A.htm?ctm_campaigntype=non_branded&gclid=EAIaIQobChMIr7_kve305QIVLCCtBh2_hg2GEAAYAyAAEgKyuPD_BwE, 2019.
Philips, Replacement Batteries and Pads for Philips HeartStart AED, https://www.usa.philips.com/healthcare/resources/landing/aed-heartstart-bls, 2004-2019.
HeartSine "Samaritan Pad-Pak Adult Cartridge", https://www.aedmarket.com/products/heartsine-samaritan-pad-pak-adult-cartridge?gclid=EAIaIQobChMImKyzjO_05QIVENRkCh01lQYQEAQYASABEgIFi_D_BwE, 2019.
Heartsine, "Pad-Pak", https://heartsine.com/product/p/pad-pak/, 2019.
International Search Report and Written Opinion dated Feb. 6, 2020 from International Application No. PCT/US19/52980.

* cited by examiner

ELECTRODE PAD CARTRIDGE FOR DEFIBRILLATORS

CROSS-REFERENCE TO RELATED APPLICATIONS

This application is a Continuation-in-Part of U.S. patent Ser. No. 16/582,920, filed on Sep. 25, 2019, which claims priority of U.S. Provisional Patent Application Nos. 62/737,032 filed Sep. 26, 2018 and 62/810,059 filed Feb. 25, 2019, all of which are incorporated herein by reference in their entirety.

FIELD

The present disclosure relates generally to replaceable electrode pad cartridges suitable for use with defibrillators.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Defibrillators are used to apply an electrical defibrillation shock to a patient that has suffered cardiac arrest. The goal of the electrical shock is to cause the patient's heart to resume beating in a normal manner Defibrillators typically include a pair of defibrillation electrode pads or paddles that are applied to a patient's chest (or the chest and back in the case of a pediatric patient) and the electrical shock passes through the patient's body between the electrode pads/paddles.

Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. AEDs are typically designed so that they can be used by a lay person in situations where professional medical help is not available. Most AEDs and some manual defibrillators use electrode pads that need to be replaced after use or after storage for a prolonged period of time. The present disclosure describes replaceable electrode pad cartridges that are well suited for use in conjunction with AEDs and other defibrillators to facilitate the easy use and replacement of defibrillation electrode pads.

SUMMARY

To achieve the foregoing and other objects, a variety of electrode pad cartridges are described that are suitable for use with a defibrillator, such as an AED.

In one aspect an AED includes one or more defibrillation electrode pads, a tray that carries the defibrillation electrode pads, the tray being slidable relative to the AED to provide access to the defibrillation electrode pads to facilitate use of the defibrillator and a presence sensor configured to detect the presence of the tray at a home position. In some embodiments, the tray carries a magnet, and the presence sensor is or includes a Hall effect sensor configured to detect a presence of the magnet to detect a presence of the tray at the home position. In some other embodiments, the tray includes a bayonet, and the sensor is or includes an optical sensor configured to detect a presence of the bayonet to detect a presence of the tray at the home position.

In some embodiments, the AED is configured to be activated when the tray is pulled from the home position. In some embodiments, the AED has a sleep or powered down mode and the presence sensor is or remains powered on when the AED is in the sleep or powered down mode. In some embodiments, the presence sensor is configured to transmit an activate defibrillator interrupt signal to at least one AED component selected from the group consisting of a defibrillator controller, a defibrillator power controller or a defibrillator activation mechanism when the presence sensor detects that the tray has been withdrawn.

In another aspect, the electrode pad cartridge includes a cartridge housing configured to be removably attached to a base defibrillator unit, first and second defibrillation electrode pads, and a tray that carries the defibrillation electrode pads. At least a portion of the tray is received within the cartridge housing such that the electrode pads are received within the cartridge housing when the tray is in a home position. The tray is configured to be pulled from the cartridge housing while the cartridge housing remains attached to the base defibrillator unit to provide access to the defibrillation electrode pads to facilitate use of the defibrillator. A presence sensor carried by the base defibrillator unit is configured to detect the tray when the electrode pad cartridge is attached to the base defibrillator unit with the tray in the home position.

In some embodiments, a security chip mounted on the cartridge housing. The security chip contains information about the electrode pad cartridge and is configured to be read by a reader on the base defibrillator unit. In some embodiments, a defibrillator controller is configured to be able to discern: (a) when the cartridge is present and properly installed on the AED; (b) when the cartridge is not present or not properly installed on the AED; and/or (c) when the tray has been slidably pulled from the cartridge housing based on information received from one or more of the presence sensor and the security chip.

The controller on the base defibrillator unit may be configured to read a variety of information and/or make a variety of determinations based on information read from the security chip. Such determinations/information may include one or more of: determining a presence of the electrode pad cartridge; determining a type of the electrode pad cartridge that is attached to the base defibrillator unit (e.g., an adult, pediatric, training, etc.); determining whether the electrode pads have been used; determine whether the electrode pads are expired or an electrode pad expiration date, etc.

In some embodiments, a defibrillator controller is configured to enter a sleep mode and the presence sensor remains powered when the controller is in the sleep mode. The presence sensor is configured to detect when the tray has been pulled from the home position while the controller is in the sleep mode and to cause activation of the defibrillator when the presence sensor detects that the tray has been pulled from the home position.

In some embodiments, the controller is configured to cause the AED to begin generating user instructions in response to the AED being activated. In some embodiments, the user instructions differ at least in part based on information read from the security chip.

In other aspects, methods of activating an AED are described. In some embodiments, while the AED is in a sleep or powered down mode, the AED detects that the defibrillator electrode pad(s) have been accessed. In response to the detection of the accessing of the defibrillator electrode pad(s), the AED is activated. In some embodiments, the AED begins generating user instructions when the AED is activated in response to the electrode pads being accessed. In some embodiments, the AED reads a type of the electrode pads that have been accessed and the instructions that are generated are based at least in part on the determined type of the electrode pads.

In another aspect the cartridge includes a cartridge housing and a tray that carries a pair of defibrillation electrode pads. At least a portion of the tray is slidably received within the cartridge housing such that the electrode pads are received within the housing. The tray is configured to be slidably pulled from the cartridge housing while the housing remains attached to the defibrillator to provide access to the electrode pads to facilitate use of the defibrillator.

In some embodiments, the tray includes at least one of a drawer box, a face plate, a pull tab and a magnet. The drawer box includes a drawer chamber that holds the electrode pads. The face plate matches a contour of the defibrillator when the electrode pad cartridge is attached to the defibrillator with the tray in a fully inserted position. The pull tab extends outward from the face plate and is configured to be gripped by a user to pull the tray out of the cartridge housing. The magnet is carried by the tray to facilitate electrical detection of the tray when the tray is seated in the cartridge housing.

In another aspect, a foil is secured to the drawer box to seal the drawer chamber. In some embodiments, the foil is heat sealed to walls of the drawer box. In some embodiments the pad tray includes an exit feature such as a channel through which electrode pad wires coupled to the electrode pads pass. The pad tray may further include a seal that cooperates with the foil to seal the exit feature. In some embodiments, a filler material that fills at least a portion of the exit feature is used as the seal and the foil is also secured to the filler material. In some embodiments, the filler material is a thermoplastic resin.

In various embodiments, the pad tray may optionally include one or more of a wire comb, a magnet and a foil pull tab. The wire comb may be positioned in the exit feature and serve to separate the wires. The magnet may be secured to the foil. The foil pull tab may be configured to be gripped by a user to facilitate tearing the foil away from at least a portion of the drawer box to provide access to the defibrillation electrode pads.

In another aspect, a security chip is mounted on the cartridge housing. The security chip contains information about the electrode pad cartridge and is configured to be read by a reader on the defibrillator. The information stored in the security chip may include one or more of a cartridge type identifier, a pad expiration date, a unique cartridge identifier, an indication of whether the pads have been used or unsealed, incident information, etc.

In yet another aspect, the cartridge housing includes a connector plug that extends outward from a top surface of the housing. The connector plug is configured to be received in a complementary recess in the defibrillator when the cartridge is installed on the defibrillator. The connector plug extends in a direction that is transverse to a direction that the tray is slidably pulled from the cartridge housing.

In some embodiments, the connector plug includes a pair of electrical contacts arranged to engage corresponding electrical contacts on the defibrillator to facilitate electrically connecting the defibrillator to the electrode pads. In some embodiments, the defibrillator contacts are spring loaded to help maintain a good electrical connection between the defibrillator and the connector plug.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Figure 1:
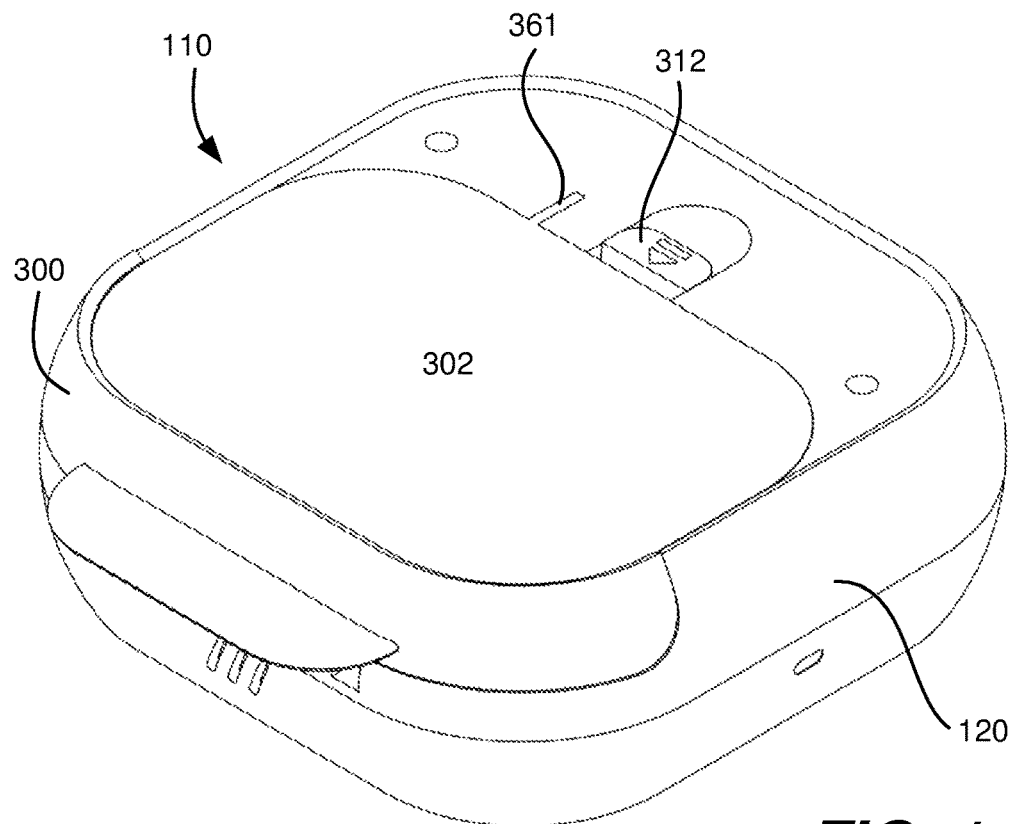
FIG. 1 is a bottom perspective view of a defibrillator having an electrode pad cartridge in accordance with a first embodiment.
Figure 2:
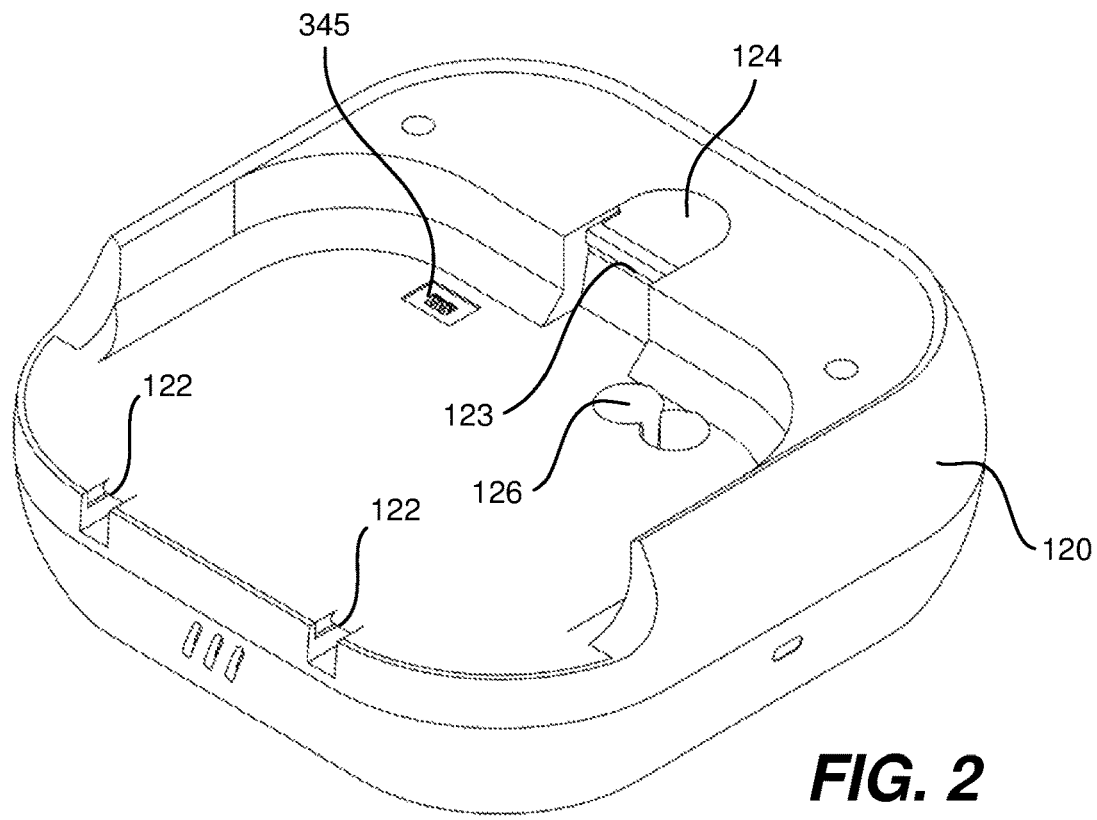
FIG. 2 is a perspective view of the base defibrillator of FIG. 1 without the electrode pad cartridge separate from the base defibrillator unit.

The present disclosure relates generally to replaceable electrode pad cartridges suitable for use with defibrillators including automated external defibrillators (AEDs). To replace the electrode pads associated with a defibrillator, a user simply removes the old cartridge (if any) and replaces it with a new cartridge. To facilitate explanation of the invention, the cartridges are described primarily in the context of embodiments in which the cartridges are used in conjunction with a defibrillator being developed by the Applicant, as illustrated in FIGS. 1 and 2. However it should be appreciated that the described cartridges may be used in conjunction with a wide variety of different types and styles of defibrillators including AEDs, manual defibrillators, hybrid defibrillators, etc.

FIG. 1 is a bottom perspective view of a modular defibrillator 100 that includes a base defibrillation unit (base unit) 110 and an optional interface unit (not shown) that is attached to the top of the base unit 110. The base defibrillation unit 110 is a fully functional defibrillator that is configured so that its functionality can be supplemented by connecting the base unit 110 to a mobile communication device (such as a smartphone, a tablet computer, etc.) having a defibrillator control app installed thereon, or by attaching an interface unit to the base unit 110. The features, components and capabilities of the defibrillator 100 may vary widely. By way of example, co-assigned U.S. patent application Ser. Nos. 16/145,657; 16/146,096 and 16/146,743 (each of which is incorporated herein by reference) describe a few such devices.

Figure 3:
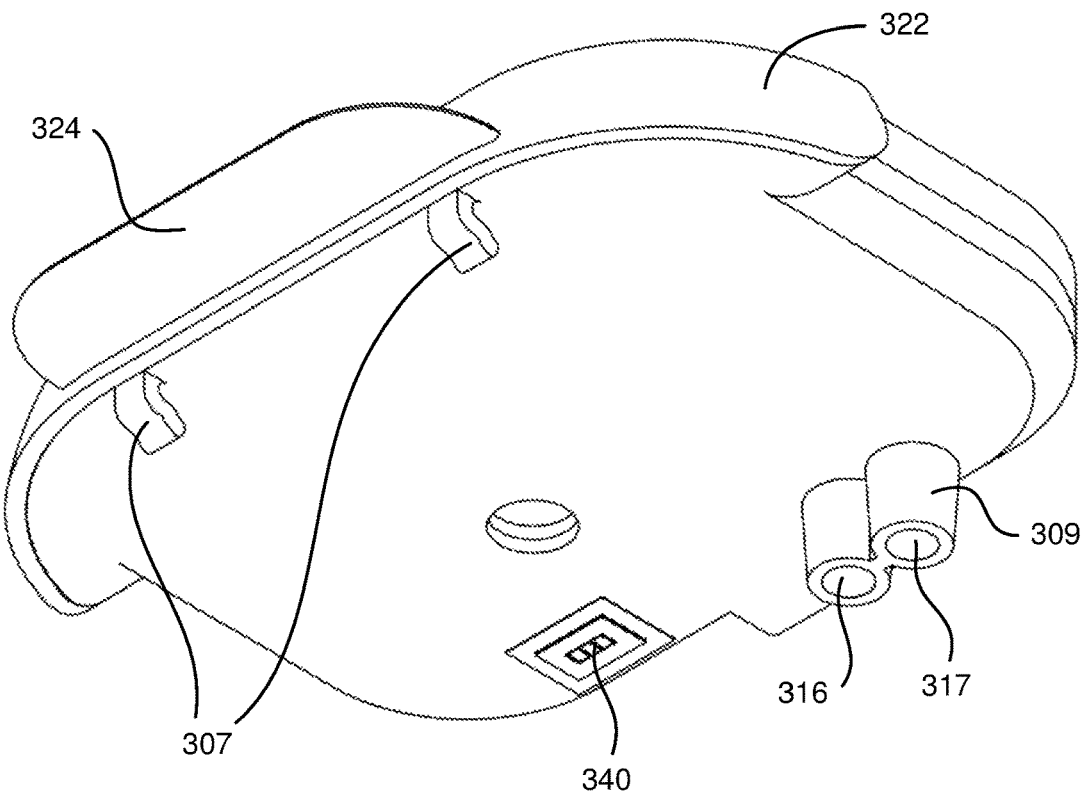
FIG. 3 is a perspective view of an electrode pad cartridge alone.

The base defibrillation unit 110 includes a base unit housing 120 that receives a replaceable electrode pad cartridge 300. The electrode pad cartridge 300 contains defibrillation electrode pads 116 therein. In FIG. 1 the cartridge 300 is secured to the bottom of base unit housing 120. FIG. 2 is a perspective view that shows the base unit 110 without a cartridge attached thereto. FIG. 3 is a perspective view of the cartridge 300 alone.

Figure 4:
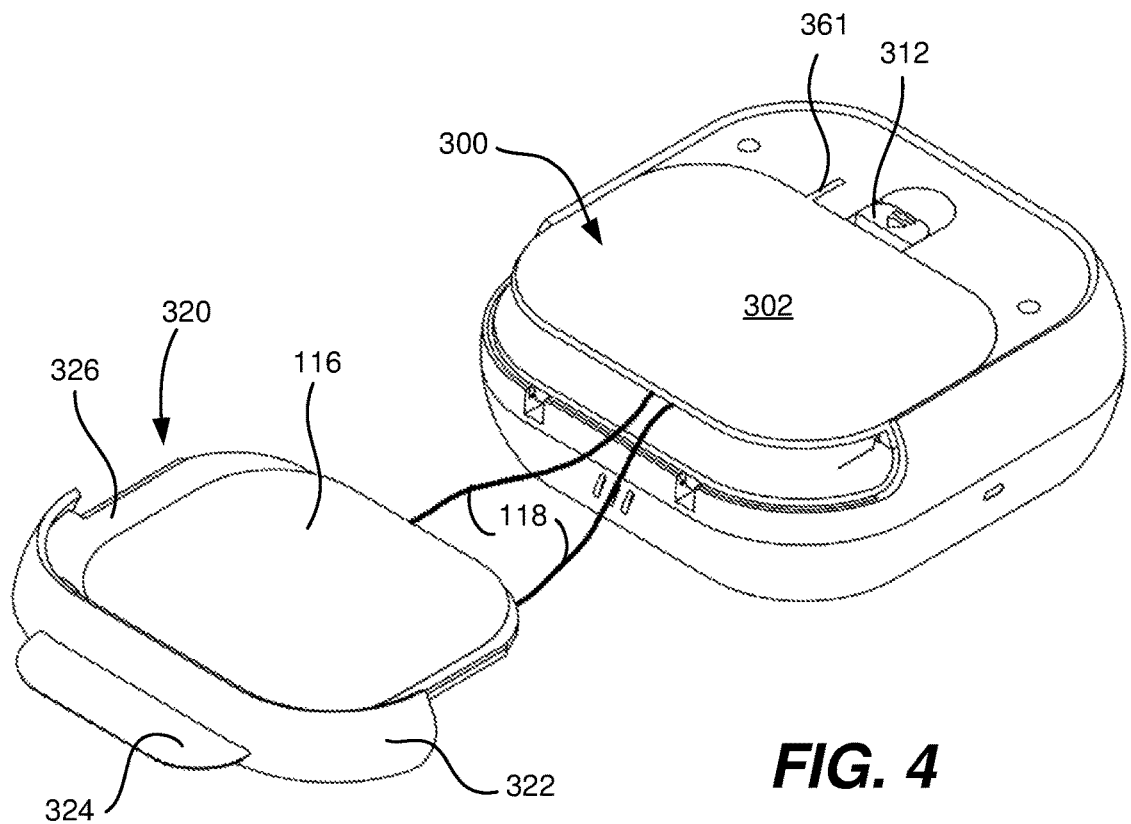
FIG. 4 is a perspective view showing a representative pad tray withdrawn from the defibrillator with the electrode pad cartridge attached to the defibrillator.
Figure 5:
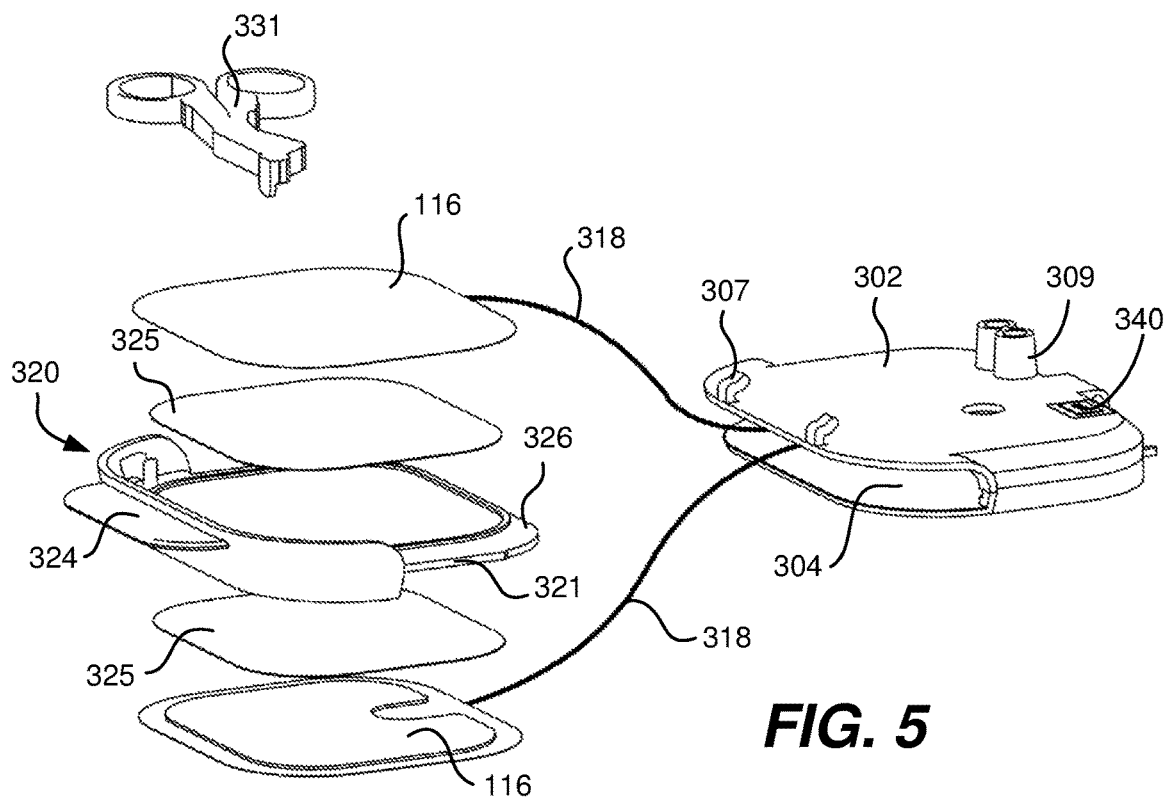
FIG. 5 is an exploded perspective view showing selected components carried by the pad tray shown in FIG. 4.

The electrode pad cartridge 300 may take a wide variety of different mechanical forms. One such structure is illustrated in FIGS. 3-5. The illustrated electrode pad cartridge 300 includes a cartridge housing 302 and a tray 320 that is slidably received by the cartridge housing 302 as best appreciated by reference to FIG. 4. In some embodiments, side edges 321 of the tray are arranged to slide into grooves or slotted rails (not shown) formed on opposing internal sides of cartridge to guide the tray into the cartridge.

The tray 320 carries an electrode pad assembly that includes a pair of defibrillation electrode pads 116 each having an associated conductor wire 318. Optionally, the tray may also carry other components that may be deemed useful during emergency use of the defibrillator such as scissors 331. In the illustrated embodiment, the tray 320 includes face plate 322, a pull tab 324 and a pad carrier 326.

The face plate 322 is sized and shaped to cover a slot opening 304 in the cartridge housing 302 and has an external surface that is generally contoured to match the shape of the base unit housing 120 when the cartridge 300 in attached to the base unit 110 with the tray 320 positioned in its home or fully inserted (closed) position as best seen in FIG. 1.

The pull tab 324 extends outward from face plate 322 so that it may be readily gripped by a user to pull the tray 320 out of the cartridge 300 while the cartridge remains attached to the base defibrillator unit 110. In some embodiments, the pull tab is labeled with appropriate text and/or graphics to help convey to a user that the tray should be pulled from the cartridge during emergency use of the defibrillator to access the defibrillation electrode pads 116. For example, the word "pull" may be printed on the pull tab and/or graphics such as arrows pointing in the direction to be pulled may be printed on the pull tab 324.

The pad carrier 326 supports the electrode pads 116 and any other desired items such as optional scissors 331. In some embodiments, a first one of the electrode pads 116 is adhered to the top surface of the pad carrier 326 and a second one of the electrode pads is adhered to the bottom surface of the pad carrier. Optionally, a release liner 325 may be provided between the pad carrier and the electrode pad. The release liner is formed from a material that the adhesive used on the bottom of the electrode pads 116 does not stick well to in order to make it easier to peel the electrode pads from the pad carrier. In other embodiments, the pad carrier 326 itself may be formed from a low stick material or may be coated with a low stick material such as silicone.

When scissors 331 or other components are included in the cartridge, the pad carrier 326 may include one or more retention feature 328, 329 to secure the scissors (or other components) to the pad carrier so that they don't jostle around when the defibrillator is handled. In the illustrated embodiment, the scissors 331 are trauma scissors and the retention features include a post 327, retention nub 328 and a small opening 329 in the pad carrier. The post 327 and retention nub 328 are configured to receive one of the scissor finger rings using a press fit. In other embodiments where the post 327 and retention nub 328 geometrically constrain a scissor finger ring, a press fit may not be necessary to retain the scissors together with the tray 320 when it is removed from the cartridge 300. The opening 329 in the pad carrier is configured to receive a tab at the distal end of one of the blades of the trauma scissors. Of course, a wide variety of other scissor (or other component) retention features can be used in other embodiments. In still other embodiments, scissor retainment can be further achieve by sticking the scissors to the cartridge 300 with a small amount of releasable adhesive at locations such as the post 327, retention nub 328, and small opening 329.

In the illustrated embodiment, the electrode pads are comprised of a main outer layer made from a polyester plastic. This layer supports a conductive foil layer, a conductive gel layer, and may support additional adhesive layers, conductive layers, and insulative layers. The polyester layer of the pad is designed to overlap, a raised ridge 334 on the pad carrier 326. The polyester layer is heat sealed to the carrier 326 thus encapsulating the conductive foil and gel layers in a sealed chamber, reducing environmental affects on the pads such as oxidation and drying, and increasing shelf life. The heat seal is broken by pulling on a tab portion of the polyester layer which is outside the heat seal. It should be appreciated that this release tab can take multiple sizes and shapes beyond the illustrated embodiment. It should also be appreciated that there are several possible layer configurations common in industry for electrode pads, and this method of sealing the electrode pads can be applied to electrode pads regardless of layer configuration.

In the illustrated embodiment, the tray 320 doesn't have side walls or a back wall at the opposite end of the pad carrier 326 as face plate 322. However, in other embodiments, the tray 320 may resemble a drawer and include side and back walls or take a variety of other forms. When a drawer type arrangement is used, both electrode pads would typically be stored within the drawer.

Figure 6:
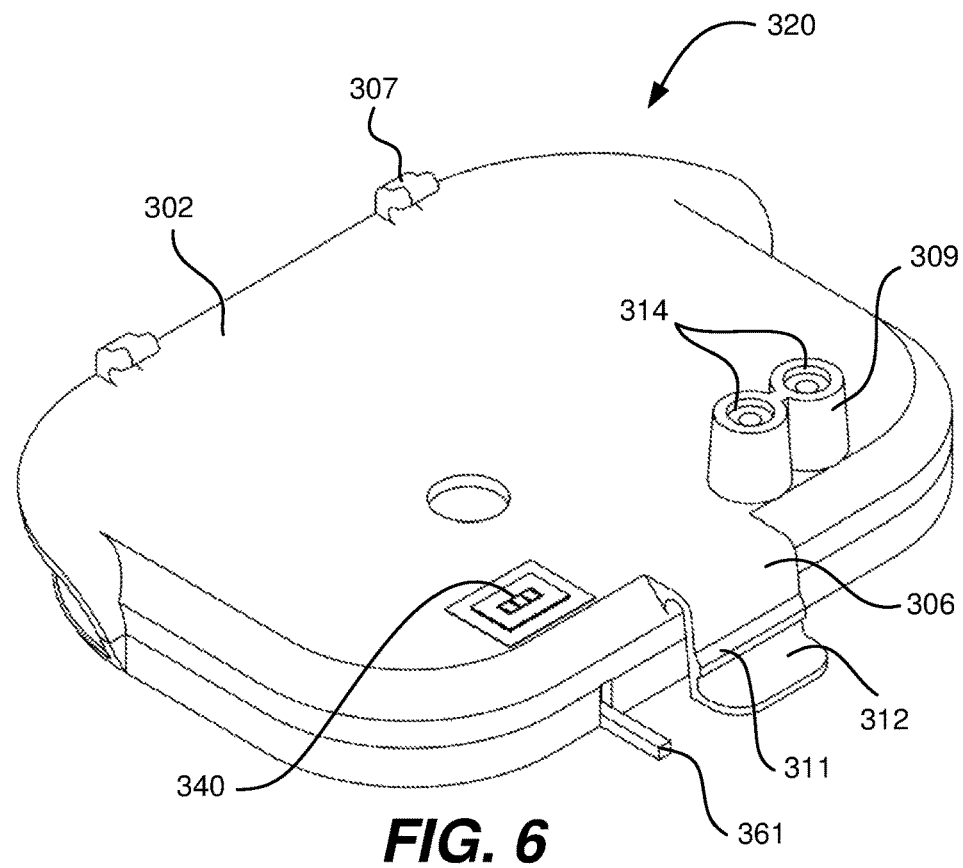
FIG. 6 is a perspective view of the cartridge housing alone.
Figure 7:
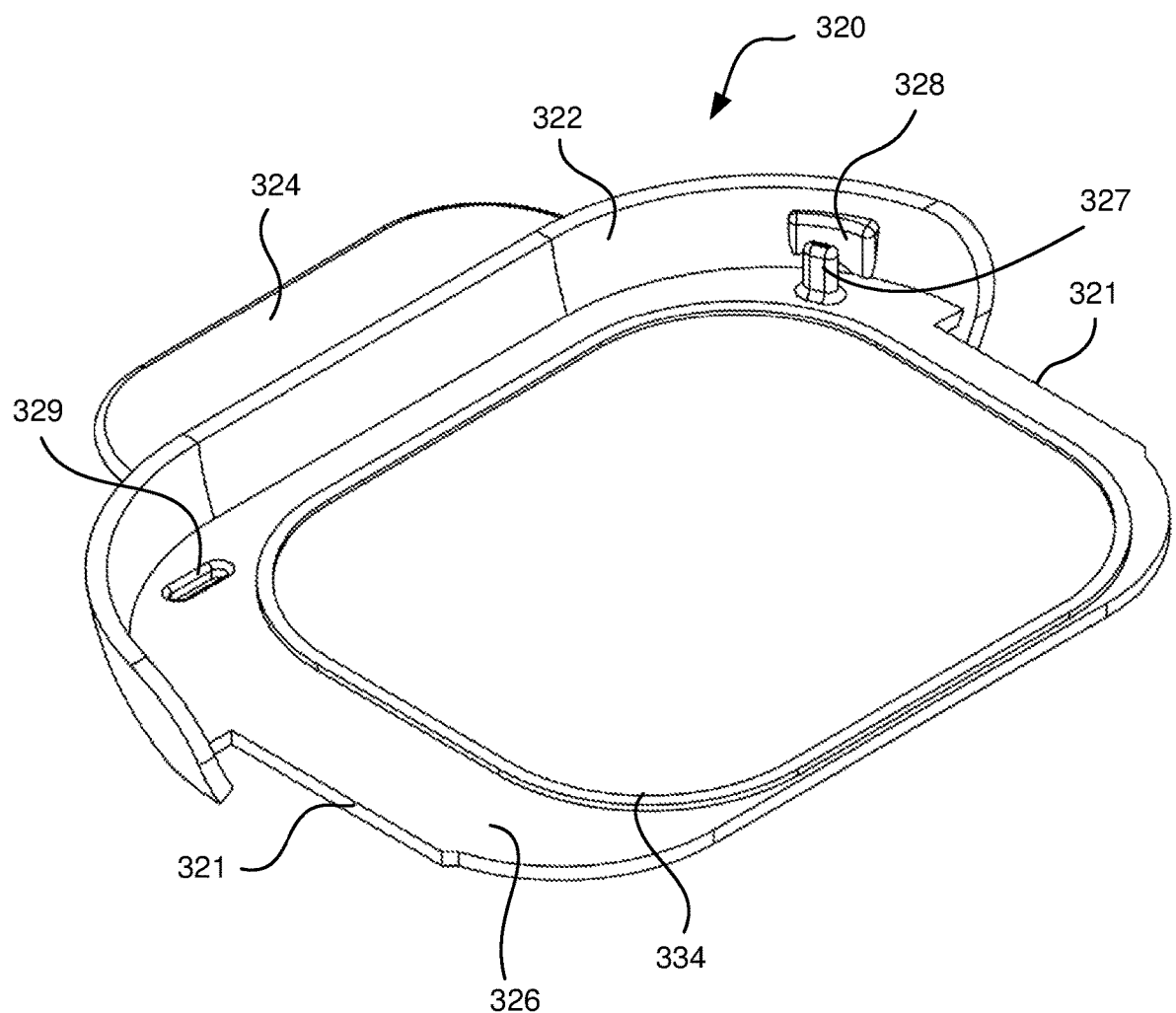
FIG. 7 is a perspective view of the pad tray of FIG. 4 alone.

The cartridge 300 is configured be detachably secured to the base unit housing 120. A wide variety of different attachment mechanisms may be used to detachably secure the cartridge to the base unit housing 120. In the illustrated embodiment, the cartridge housing 302 includes a latch 306, a pair of hooks 307, and connector plug 309, as best illustrated in FIG. 6.

The hooks 307 are located near the front face of the cartridge housing 302 and are configured to hook onto catch features (e.g. shelves 122 or bars) in the base unit housing 120 when the cartridge is attached to the base unit housing. The latch 306 extends from the back face of the cartridge housing and includes a projection 311 and a tab 312. The projection 311 is a catch feature that engages a mating catch feature (e.g. bar 123 seen in FIG. 2) in the base unit housing. The latch itself 306 serves as a flexure that presses the projection 311 into engagement with the trough 123. Thus, the latch 306 and hooks 307 cooperate to hold the cartridge in place when the cartridge is attached to a defibrillator. The tab 312 is positioned over a finger recess 124 in the base unit housing 120. The latch, and thus the cartridge 300 can be released by pulling on the tab 312 to release the projection 311 from a trough formed above bar 123. In some embodiments there may be multiple of these latch/retention features to add additional mechanical stability to the design. Where one latch/retention features requires user input at one point, multiple latch/retention features require multiple user input to release, reducing the likelihood of unintentional cartridge release, while also increasing the overall mechanical strength of the total combined latches.

Figure 8:
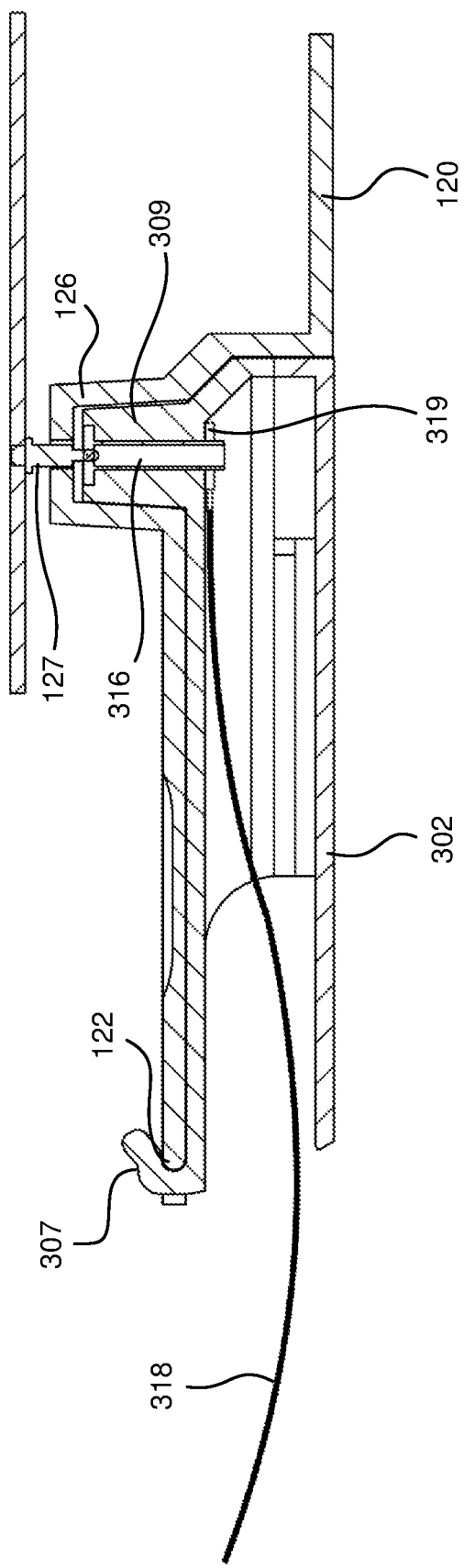
FIG. 8 is a diagrammatic cross sectional view of a cartridge/defibrillator housing interface highlighting an electrical connection between the cartridge and the base defibrillator unit.

The connector plug 309 extends upward from a top surface of the cartridge housing 302 and is configured to be slid into connector well 126 in the base unit housing. Thus, the connector plug 309 and the connector well 126 cooperate to form an alignment feature that helps align the cartridge when coupling cartridge 300 to the base unit housing. The connector plug includes a pair of receptacles 314 that each contains an electrical contact post or rivet 316, 317. As best illustrated in FIG. 8, in some embodiments, the electrical contact posts 316, 317 take the form of brass rivets having enlarged heads. The contact rivet heads are configured to engage electrical contact 127 and 128 on the base unit 110 when the cartridge 300 is installed on the base defibrillator unit. The contact posts act as a conduit between the electrical contacts 127, 128 and the electrode pad wires 318 which are stored inside the cartridge 302. In some embodiments, the electrical contacts 127 and 128 on the base unit include robust spring loaded connectors (as for example pogo pin connectors) to help ensure that a good electrical connection is made between on the base unit's electrical contacts 127, 128 and the cartridge's contact posts 316, 317.

Each contact post 316, 317 to also electrically connected to an associated one of the electrode pad wires 318. The nature of the connection may vary. For example, when the contact posts take the form of rivets, each electrode pad wire 318 may have a ring terminal 319 at its proximal end that is engaged by the splayed tail portion of the associated contact rivet when the rivet is compressed to form a strong mechanical connection and a robust electrical connection between the rivets and the defibrillation pad assembly.

Each base unit electrical contact 127, 128 is connected to the appropriate base unit electronics (e.g., high voltage shock discharge circuitry, low voltage EKG sensing circuitry, etc.). Therefore, plugging connector plug 309 into connector well 126 electrically connects the defibrillation electrode pads 116 to the appropriate base unit electronics. The described rivet and spring loaded/pogo pin connectors are well suited for use in connecting the electrode pads to the defibrillator because they are well suited for both (a) handling the very high voltage/power discharges utilized in defibrillation shocks; and (b) conducting the precise signals associated with EKG sensing, and c) maintaining electrical connection in high-vibration environments which might otherwise disrupt signal transfer. Although the described connectors work well, it should be appreciated that a variety of other connector structures can be used in alternative embodiments.

In some embodiments, the cartridge 300 also includes a security chip 340 and the base unit 110 includes a chip reader 345. In the illustrated embodiment, the security chip (memory) is mounted on the exterior of the cartridge housing 302 well apart from the connector plug 309 to help isolate it from the high voltage conduction path to the pads during discharge of the defibrillator. The security chip is configured to store information about the cartridge 300 that may be useful for the defibrillator. The chip reader 345 is configured to read the security chip and communicate such information to the defibrillator controller. A wide variety of different types of information can be stored on the security chip. By way of example, the stored information can include information indicative of one or more of: (a) the type of pads stored within the cartridge; (b) the model and/or manufacturer of the pads; (c) a serial number or other identifier that uniquely identifies that cartridge; (d) the pads expiration date; (e) the date of manufacture, manufacturing lot number or other information about the manufacture of the cartridge; or (f) any other information of use or interest.

These types of information can be useful to the defibrillator and/or the management of the defibrillator in a variety of different ways. For example, there are several types of electrode pads that may be used in conjunction with a defibrillator. Common pad types include adult pads, pediatric pads, universal pads and training pads. Identifying the pad type allows the defibrillator to function differently, or render different instructions, as appropriate based on the type of pad that is in use. For example, when training pads are in use, it may be desirable to not charge the defibrillator's discharge capacitor when the defibrillator is activated and/or not actually deliver a shock. In another example, if the defibrillator is stored with training pads in place instead of pads intended for use, the defibrillator's owner or administrator can be warned of the situation and advised to replace the training pad cartridge with a cartridge having electrode pads intended for emergency use. In another example, some defibrillators distinguish between adult pads and pediatric pads and may be configured to operate differently or warn an operator based on the type of pads used.

Information about the expiration date of the electrode pads may be used to confirm whether the attached pads are suitable for use or to facilitate warning the defibrillator's owner or administrator when it's time to replace the electrode pad cartridge 300. Some of the other information can be useful for quality control, tracking and/or other purposes.

In some embodiments, the chip reader 345 also has writing capabilities. When writing capabilities are available, the defibrillator controller can be configured to store selected information (e.g. pad history) in the cartridge. Again, a wide variety of different useful information can be stored on the cartridge in this manner. For example, information regarding whether/when the tray has been pulled from the cartridge, and/or whether/when the pads have been removed from the carrier may be stored on the security chip. In another example, the defibrillator may be configured to perform periodic status checks that verify that electrode pads are attached and/or are in good operational condition. When desired, the results of such tests (or other defibrillator status checks) may be stored on the security chip. Such information can be useful for quality control, reporting, monitoring and/or other purposes if/when the cartridge is recycled or otherwise returned to its producer. In yet another example, if desired, selected incident information can be stored on the cartridge as well if and when the defibrillator is used in an emergency incident. Again, this can be useful for reporting, device monitoring and other appropriate purposes.

Figure 9:
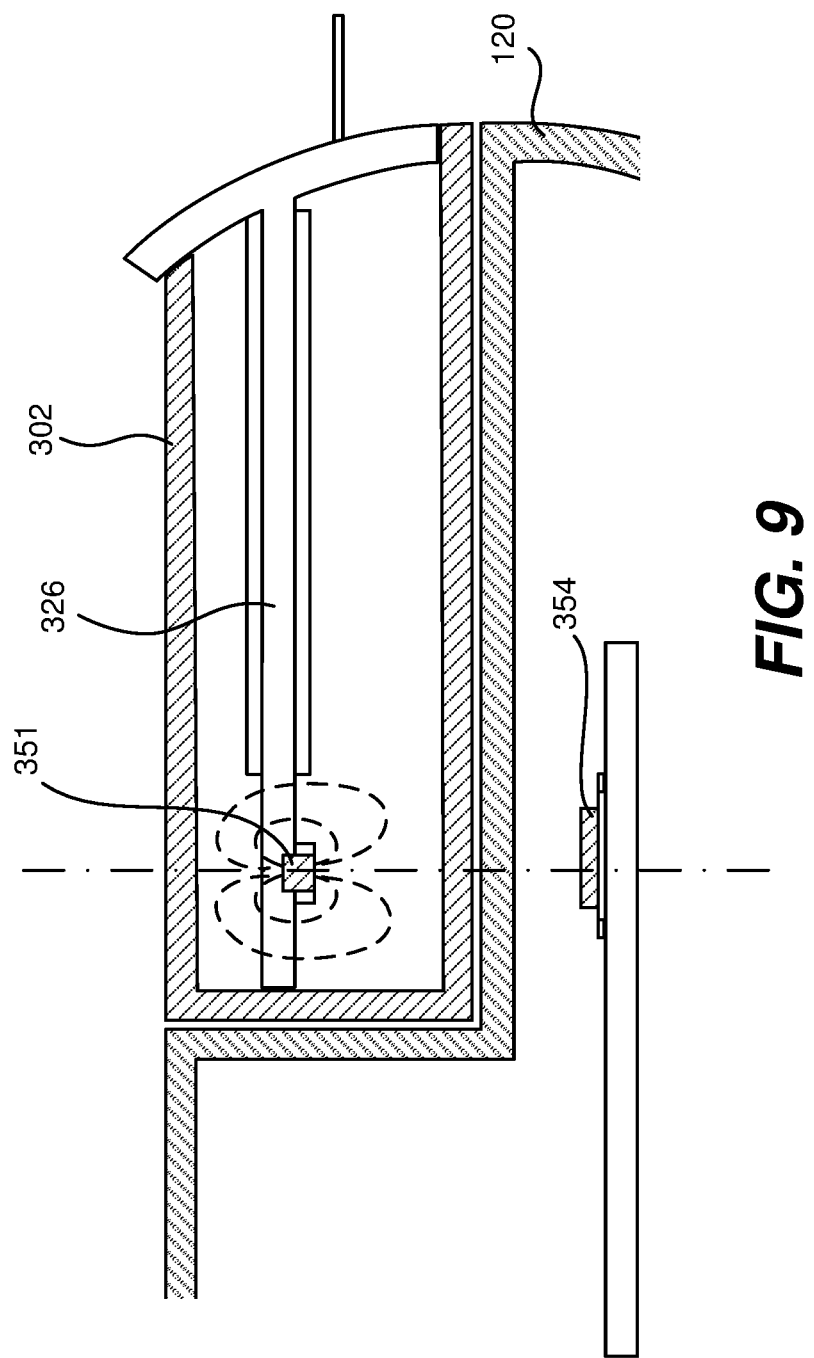
FIG. 9 is a diagrammatic cross sectional view of a cartridge/defibrillator housing interface highlighting a presence sensor for detecting the presence of a pad cartridge.

In some embodiments, the base unit also has one or more sensors configured to detect the presence of the cartridge and/or removal of the tray from the cartridge. A variety of sensors can be used for such purposes. By way of example, various optical or Hall Effect sensors are well suited for such tasks. In one particular embodiment illustrated in FIGS. 4 and 6, the pad carrier tray includes a bayonet 361 that extends outward from the back end of pad carrier 326. When the tray 320 is in its home position fully inserted into the cartridge housing 302, the bayonet 361 protrudes through an opening in the back wall of cartridge housing 302. An optical sensor mounted on the base unit can be used to detect the presence of a bayonet 361 when a cartridge is inserted into the defibrillator. When the tray 320 is pulled from the cartridge housing 302, the bayonet no longer extends through the back wall and its absence can be detected the optical sensor. In other embodiments, the bayonet can carry a small magnet whose presence or absence can be detected by a Hall Effect sensor mounted on the base unit 110. In other embodiments there is no bayonet feature, and a small magnet 351 is embedded in the plastic of the pad carrier 326, and thus the presence or absence of the pad carrier can be detected by a Hall effect sensor 354 mounted on the base unit 110 as diagrammatically illustrated in FIG. 9. Of course, a wide variety of other presence sensors 354 and sensing arrangements can be used to detect the presence of a cartridge 300 and/or the tray within the cartridge.

In some embodiments, the AED is configured to be activated (powered on) when the tray insert 320 is pulled from the cartridge 300. To facilitate such a structure, the presence sensor 354 is powered even when the defibrillator controller is placed in a sleep mode or is powered down. When the presence sensor detects that the tray insert has been withdrawn from the cartridge, it sends and appropriate activate defibrillator interrupt to the defibrillator controller, a power controller that controls power to the defibrillator electronics or other suitable defibrillator activation mechanism. When a power controller is used, the power controller, in turn activates the defibrillator controller and any other electrical components that need to be powered.

Figure 10:
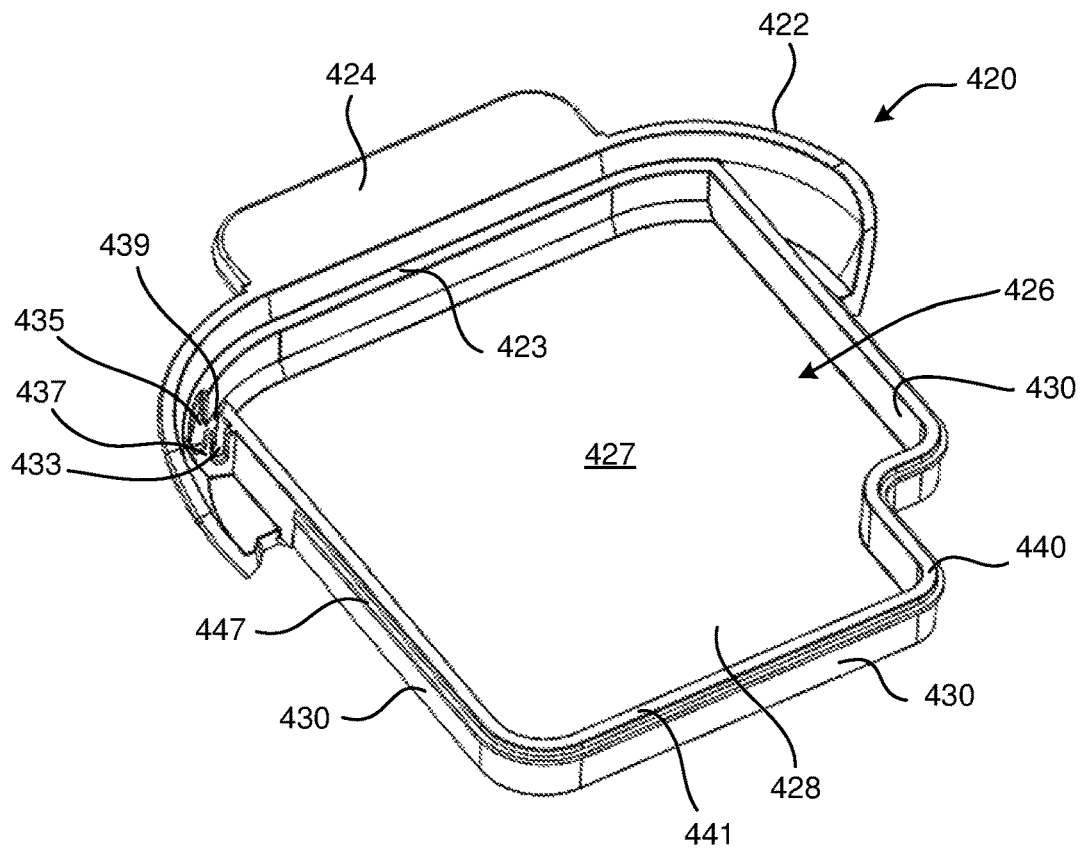
FIG. 10 is a perspective view of a drawer style pad tray in accordance with another embodiment.
Figure 11:
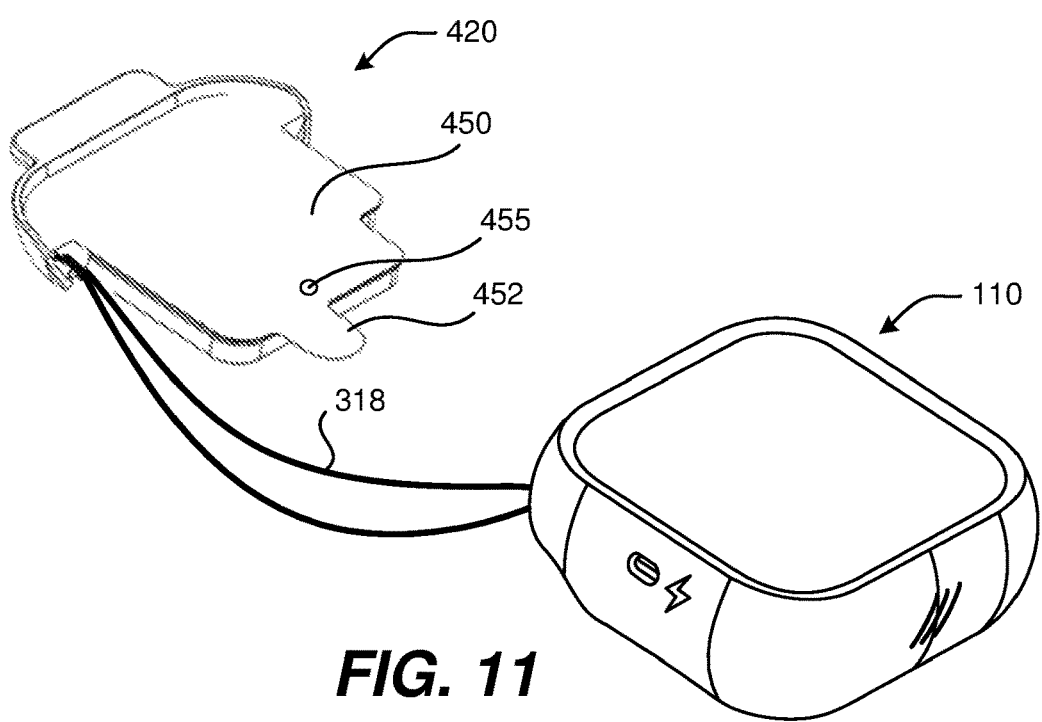
FIG. 11 is a perspective view of the pad tray of FIG. 10 with a foil seal secured thereto with a defibrillator.

Referring next to FIGS. 10-11 an alternative drawer style pad tray 420 will be described. In this embodiment the pad tray 420 includes a face plate 422, pull tab 424, a drawer box 426, wire channel 435 and wire comb 437. The drawer box 426 includes drawer bottom 428 and drawer walls 430 that extend upward around the periphery of the drawer bottom. The exposed upper edges 440 of the drawer side walls 430 forms a sealing surface 441. The inner side of face plate 422 includes a ledge 423 at the same height as the upper edges 440 of the drawer walls 430. The ledge 423 serves as another sealing surface and cooperates with the drawer wall sealing surfaces 441 to form sealing surfaces substantially around the periphery of a drawer chamber 427 configured to hold the electrode pads 116. In the illustrated embodiment the ledge 423 is effectively the top end of a drawer wall that is integrally formed with the face plate.

A wire opening 439 is formed in one of the drawer walls 430 to serve as a port through which the electrode pad wires 318 may pass. In the illustrated embodiment, the wire channel 435 is formed between an inner segment of the face plate 422 and a facing outer segment of one of the drawer walls. The wire comb 437 is positioned at one end of the wire channel 435. The wire comb 437 includes a pair of slots 438 that are each sized to receive one of the electrode pad wires 318. The wire comb 437 forms an exit feature through which the electrode wires exit the wire channel 435 and ultimately the pad tray 420.

Figure 12:
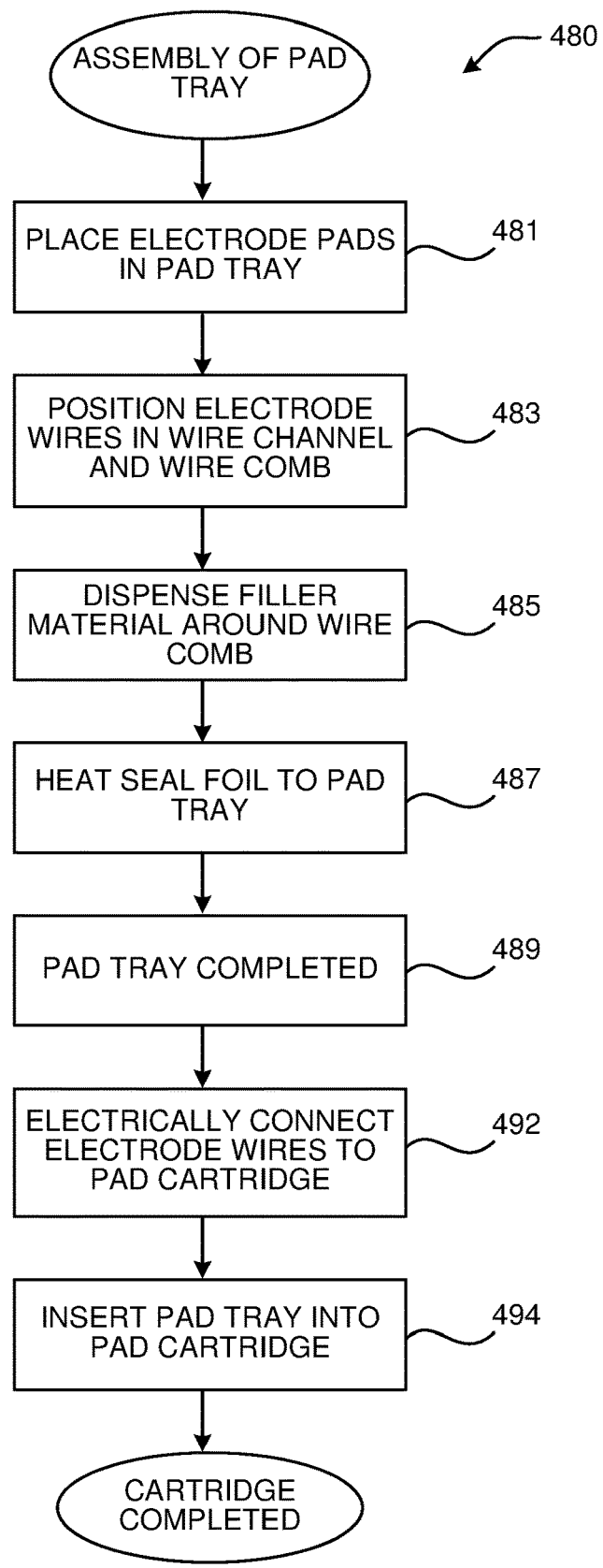
FIG. 12 is a flow chart illustrating a process of assembling a pad tray.

Referring in parallel to the flow chart of FIG. 12, during assembly of the pad tray 420, the electrode pads 116 are placed in the drawer chamber 427 of the pad tray as represented by block 481. The electrode pad wires 318 are positioned so that they exit drawer chamber 427 through wire opening 439 and wire channel 435. Each wire 318 is placed in a corresponding one of the comb slots 438. Thus, the wire comb 437 serves to align and separate the electrode pad wires 318 and generally hold the wires in position.

After the electrode pads and wires have been placed, a filler material (not shown) is dispensed in the wire channel 435, surrounding the electrode wires and filling the wire channel 435 to a level generally planar with the upper edges 440 of drawer walls. (Block 485). This effectively seals the wire channel 435 with the electrode wires in place. A variety of materials can be used as the filler—as for example a hot melt material such as a thermoplastic resin. In other embodiments, epoxy or various other materials can be used as the filler. In some embodiments a mold that fits over the wire channel 435 is used and the filler material is injected into the mold, effectively filling the wire channel 435. In other embodiments, a grommet on the wire or other suitable sealing structure may be used in place of the filler material.

After the filler has been dispensed, a foil 450 is secured to the sealing surfaces 423, 441 of drawer box 426 via heat sealing. (Block 487). The foil preferably covers the entire drawer chamber 427 and at least the portion of the wire channel 435 from the wire opening 439 to the wire comb 437. In the illustrated embodiment the foil has a left ear portion that covers this section. A complementary right ear portion covers a corresponding segment on the opposite side of drawer box 425, however that is not a requirement. In other embodiments, each electrode wire, or other wires, can exit from separate wire channel features, each channel being covered by the foil to create a heat seal.

The filler material is preferably formed from a material such as thermoplastic resin that the foil can also be adhered to via heat sealing. Thus, the electrode pads are sealed within the drawer chamber. Sealing the tray in this manner can help mitigate drying of the pad's conductive gel, which can potentially prolong the useful working lives of the electrode pads. The foil 450 may include a pull tab 452 that extends beyond the footprint of the drawer box 426 as best seen in FIG. 11. The pull tab 452 is configured to be pulled by a user to remove the foil 450 from the drawer box, thereby exposing the defibrillation pads 116.

After the pad tray has been completed (block 489), the free ends of electrode wires 318 are electrically coupled to the cartridge (block 492) as will be described in more detail below. In other embodiments, the free ends of the electrode wires can be electrically coupled to the cartridge before the wires have been sealed in the tray 420. After the electrode wires are connected, the pad tray is inserted into the pad cartridge (block 494). In the embodiment of FIG. 10, side ribs 447 are provided on the outer side of drawer walls 430. The side ribs (rails) are arranged to slide into grooves or slotted rails (not shown) formed on opposing internal sides of cartridge to guide the tray 420 into the cartridge. In the illustrated embodiment, the rib 447 extends continuously around the lateral and back sides of the drawer although that is not a requirement. For example, the side ribs 447 may be provided only on the lateral side walls of the pad tray and not on the back surface. Of course, a variety of other alignment structures including slots and other suitable mechanism can be used in place of the described ribs.

In the event of an emergency use of the defibrillator, the user (rescuer) pulls on tray pull tab 424 to remove the pad tray 420 from the defibrillator/pad cartridge. This state is shown in FIG. 11. At this stage, the pad tray remains sealed. As such, the pad tray may be reinserted into the cartridge if it was inadvertently removed. To use the defibrillator, the user then removes the foil, which can be accomplished by pulling up on foil pull tab 452. The heat seal that secures the foil to the pad tray is preferably a relatively weak attachment so that the foil can readily be torn away from the drawer box 426.

The pads are then removed from the tray and may be used in a conventional manner. In some implementations, the defibrillation electrode pads may be adhered to a release liner that is removed before placing the pads on a patient's chest for use. Alternatively or additionally, in some embodiments the pads may be placed in a sealed pouch that is removed prior to use. However, it is pointed out that the sealing of the drawer chamber 427 described above can reduce or eliminate the incentive to place each pad in a single sealed pouch as is somewhat common in the industry.

In some embodiments, a magnet 455 is attached to the top surface of foil 450. A Hall Effect sensor (not shown) on the base unit housing is positioned adjacent the location that the magnet 455 will be in when a cartridge 500 having a sealed pad tray 420 therein is installed on the base unit. When the tray is pulled out of cartridge 500, the magnet moves away from the Hall Effect sensor, thereby providing a mechanism to determining when the tray has been removed. Specifically, the magnetic field detected by the Hall Effect sensor will change when the pad try 420 is removed. If an undisturbed/unused tray is subsequently reinserted back into cartridge 500, the defibrillator can determine that the unused tray has been reinserted. Alternatively, if the foil has been removed or otherwise disturbed due to use of the electrode pads, the magnet would not be in the same position (if it is present at all) and thus the defibrillator can determine that the pads have been tampered with and should be treated as used. In some embodiments, the magnet 455 is positioned close to the foil pull tab 452 since the pull tab is expected to be the location from which the foil is detached from the drawer walls. With this positioning, disturbances of the foil are more easily and reliably detected.

In some embodiments, detection of the removal of the tray serves as a mechanism for turning on the defibrillator. Alternatively or additionally, detection of the removal of the tray may also trigger any desired notifications—as for example, initiating a message that is sent or relayed to a server indicating that the defibrillator has been activated, that the pads need to be replaced, etc.

Figure 13:
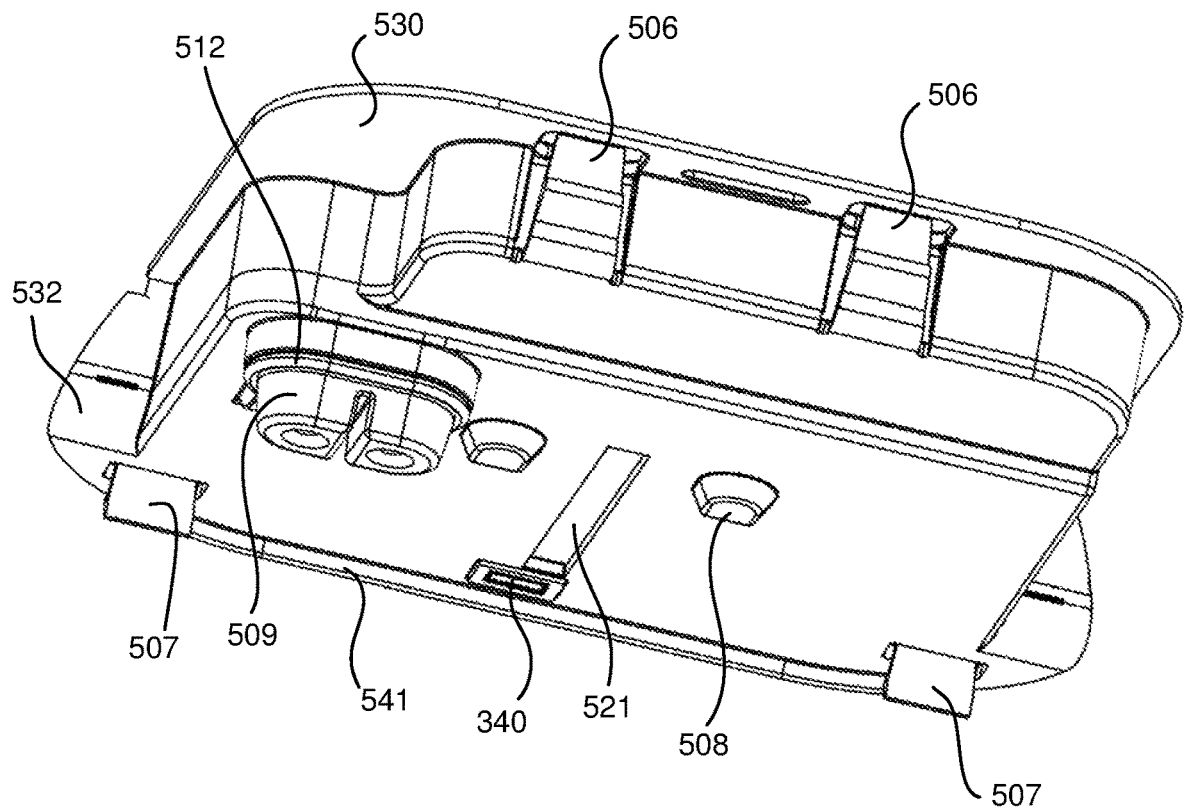
FIGS. 13-15 are perspective views of an alternative defibrillation pad cartridge housing.
Figure 14:
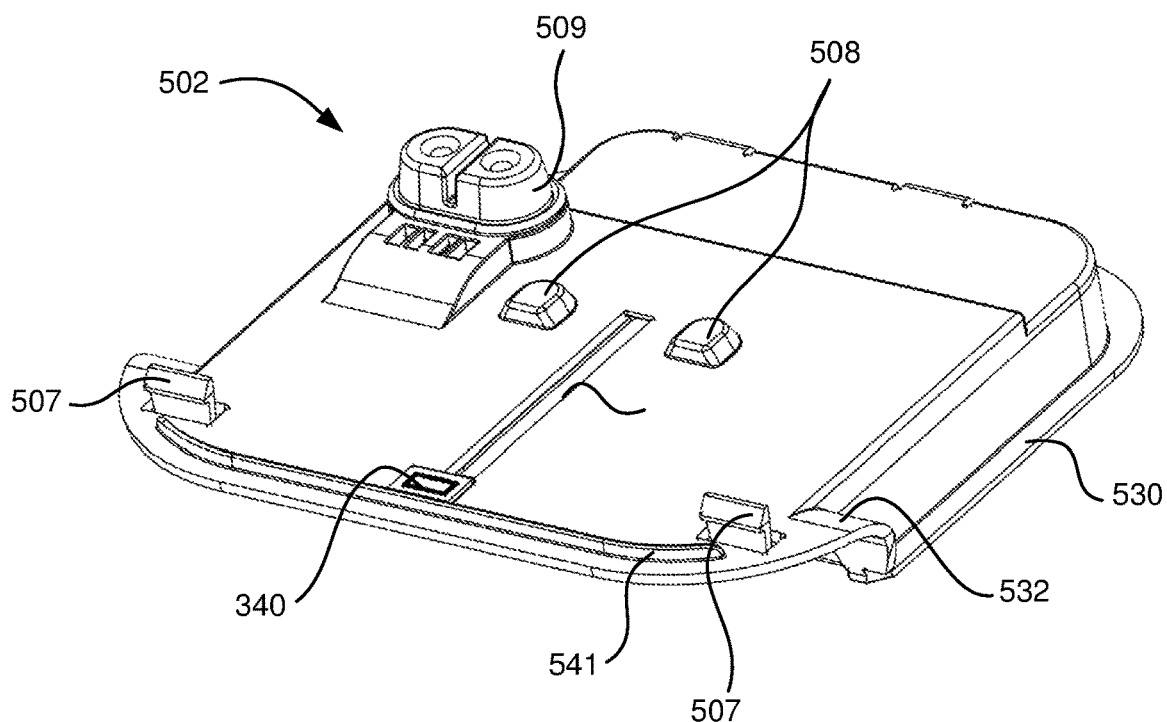
Figure 15:
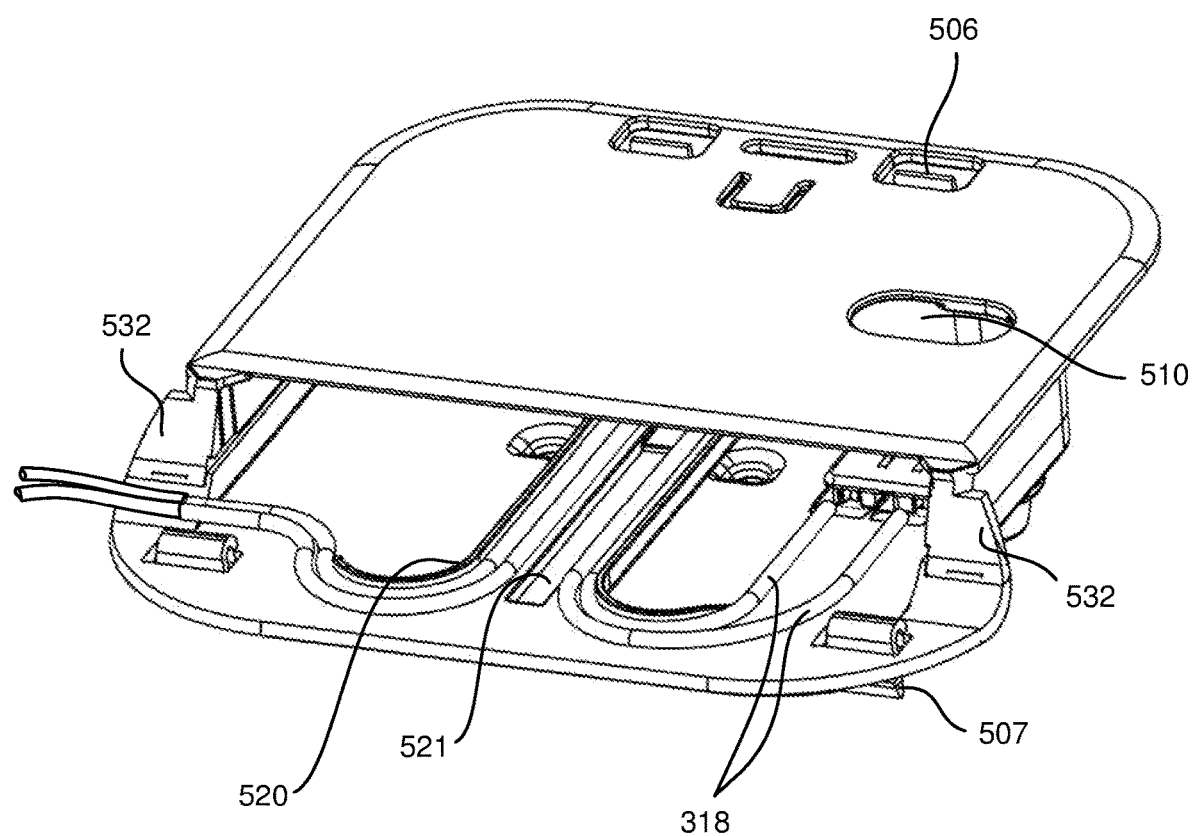

Referring next to FIGS. 13-15, an alternative cartridge housing 502 will be described. In the illustrated embodiment, the cartridge housing 502 includes a pair of rear latches 506, a pair of front latches 507, a pair of alignment bosses 508, a connector plug 509, a connector access opening 510, a security chip 340, a wire guide 520, a wire access slot 521, a base flange 530 and front face flanges 532. FIG. 15 additionally shows the placement of connected ends of the electrode pad wires 318.

The cartridge 500 is configured to snap into mating features on the bottom of the base defibrillator unit housing 120 via latches 506 and 507. In the illustrated embodiment, the latch features 506 and 507 include flexures that are designed to engage catch features on the defibrillator unit housing. However, in alternative embodiments, the flexures can be on the defibrillator unit housing with the latch features themselves being catch portions of the latches. The alignment bosses 508 and connector plug 509 help align and position the cartridge during insertion and help provide lateral stability after insertion. The connector plug 509 extends upward from a top surface of the cartridge housing 302 and is configured to be slid into a complimentary connector well in the base unit housing. The connector plug 509 and the complementary connector well housing may be similar to connector plug 309 or may take a variety of other forms. Connector access opening 510 provides access to the connector plug 509 during assembly and provides access for riveting the contact posts to the ring terminals of the electrode pad wires 318. For example, during assembly, a rivet press may be inserted through the connector access opening 510 to rivet the contact posts to the ring terminals (step 492 of FIG. 12).

In some embodiments, an O-ring 512 is provided on the connector plug boss to help seal the defibrillator.

Optional wire guide 520 is provided to help manage the positioning of electrode wires 318. One end of each wire 318 is connected to a corresponding electrode pad 116 and the other end is connected to a corresponding contact post on connector plug 509. Typically there will be some portion of the electrode wires (e.g., 5-10 inches) that is positioned outside of the pad tray to facilitate connecting the wires to the connector plug. It is helpful to ensure that the portion of the electrode wire that is outside of the pad tray 420 doesn't get in the way of pad tray insertion after the electrode wires have been connected to the connector plug. The wire guide 520 provides a mechanism for defining the wire routing. When the pad tray is inserted, a tool may be inserted through wire access slot 521 to pull the wires inward within the constraints of wire guide 520, which positions the proximal end of the wire in a defined location. When the tray is removed, the wire guide 520 doesn't interfere with the withdrawal of either the tray or the electrode wires themselves.

The security chip 340 is mounted on the top surface of the housing and is positioned to be read by a chip reader on the base unit 110 as discussed above. Although a particular position is shown, it should be appreciated that the actual position of the security chip on the cartridge housing can be widely varied. In some embodiments, a rib 541 is provided adjacent the security chip 340 to increase the rigidity of the upper wall of cartridge housing 502 in the region of the security chip. This helps ensure a good electrical connection between the security chip 340 and the chip reader 345. In some embodiments, the rib 541 is received by a mating recess in the defibrillator housing floor which further helps hold the cartridge in place laterally and longitudinally. As described above, the security chip 340 provides a mechanism that the defibrillator controller can use to determine whether an authorized cartridge is attached. Thus, with the described embodiment, the defibrillator can determine both (a) the presence (or absence) of a pad cartridge 500 (by detecting the presence of security chip 340); and (b) whether the valid pad tray is present (through the output of the Hall Effect sensor which detects the magnet 455 on pad tray foil 450). The security chip may include the types of information discussed above with respect to other embodiments. Furthermore, the security chip may include information regarding whether the pads tray has been opened or unsealed.

In some embodiments, the cartridge housing 502 includes a base flange 530 that serves as a registration surface against the bottom of the defibrillator housing when the pad cartridge 500 is inserted into the defibrillator. The cartridge housing also includes front face flanges 532 which serve as registration surfaces as well. The inner surfaces of front face flanges 532 register against the defibrillator housing. The outer surfaces of front face flanges 532 register against the pad tray face plate 422 when the pad tray is inserted into the cartridge.

Although only a few embodiments of the invention have been described in detail, it should be appreciated that the invention may be implemented in many other forms without departing from the spirit or scope of the invention. For example, the tray structure, the cartridge geometry and latching mechanisms and the components carried on the tray may all vary widely with the needs of any particular defibrillator system. Some defibrillators utilize more than two defibrillation electrodes or include other types of sensing electrodes. When used, the additional electrodes can also be carried on the tray or within a drawer that is withdrawn in a manner similar to the described tray. In some implementations the electrode pads may be part of a unitary or larger structure that carries both of the electrodes, as for example being connected by webbing, as part of a bib, a carrier material, etc.

The geometry of the electrode cartridge 300 may vary widely to conform with the needs of any particular defibrillator. In some embodiments, a gasket or seal may be provided on the inside surface of the face plate to provide a watertight or waterproof seal around the cartridge slot opening 304. Additional gaskets or seals may be proved around any other cartridge openings, or opposite such openings to make those openings water resistant as well.

In the primary embodiments described above, the pad trays 320, 420 are configured to slide into a cartridge (e.g., cartridge housing 302, 502). However, it should be appreciated that in alternative embodiments, the same type of pad tray can effectively serve as the cartridge and be inserted directly into a pad tray chamber in the defibrillator housing without requiring the use of a higher level cartridge.

From the foregoing, it should be apparent that the present embodiments should be considered illustrative and not restrictive and the invention is not to be limited to the details given herein, but may be modified within the scope and equivalents of the appended claims.

What is claimed is:

1. An automated external defibrillator (AED) comprising:
   first and second defibrillation electrode pads;
   a tray that carries the defibrillation electrode pads, the tray being slidable relative to the AED to provide access to the defibrillation electrode pads to facilitate use of the defibrillator; and
   a presence sensor configured to detect the presence of the tray at a home position relative to the AED.

2. An AED as recited in claim 1 wherein the tray carries a magnet, and the sensor is or includes a Hall effect sensor configured to detect a presence of the magnet to detect a presence of the tray at the home position relative to the AED.

3. An AED as recited in claim 1 wherein the tray includes a bayonet, and the sensor is or includes an optical sensor configured to detect a presence of the bayonet to detect a presence of the tray at the home position.

4. An AED as recited in claim 1 wherein the AED is configured to be activated when the tray is pulled from the home position.

5. An AED as recited in claim 1 wherein the AED has a sleep or powered down mode and the presence sensor is or remains powered on when the AED is in the sleep or powered down mode.

6. An AED as recited in claim 1 wherein the presence sensor is configured to transmit an activate defibrillator interrupt signal to at least one AED component selected from the group consisting of a defibrillator controller, a defibrillator power controller or a defibrillator activation mechanism when the presence sensor detects that the tray has been withdrawn.

7. An automated external defibrillator (AED) comprising:
   a base defibrillator unit;
   an electrode pad cartridge configured for attachment to the base defibrillator unit, the electrode pad cartridge including a cartridge housing configured to be removably attached to the base defibrillator unit, first and second defibrillation electrode pads, and a tray that carries the defibrillation electrode pads, wherein at least a portion of the tray is received within the cartridge housing such that the electrode pads are received within the cartridge housing when the tray is in a home position, the tray being configured to be pulled from the cartridge housing while the cartridge housing remains attached to the defibrillator to provide access to the defibrillation electrode pads to facilitate use of the defibrillator; and
   a presence sensor carried by the base defibrillator unit, the presence sensor being configured to detect the tray when the electrode pad cartridge is attached to the base defibrillator unit with the tray in the home position.

8. An AED as recited in claim 7 further comprising a security chip mounted on the cartridge housing, wherein the security chip contains information about the electrode pad cartridge, the security chip being configured to be read by a reader on the base defibrillator unit.

9. An AED as recited in claim 8 wherein the controller is configured to be able to discern: (a) when the cartridge is present and properly installed on the AED; (b) when the cartridge is not present or not properly installed on the AED; and (c) when the tray has been slidably pulled from the cartridge housing based on information received from one or more of the presence sensor and the security chip.

10. An AED as recited in claim 7 wherein:
    the base defibrillator unit includes a controller configured to enter a sleep mode; and
    the presence sensor remains powered when the controller is in the sleep mode and the presence sensor is configured to detect when the tray has been pulled from the home position while the controller is in the sleep mode and to cause activation of the AED when the presence sensor detects that the tray has been pulled from the home position.

11. An AED as recited in claim 7 wherein the AED is configured to be activated when the AED is in a sleep mode and the presence sensor detects that the tray has been moved from the home position.

12. An AED as recited in claim 7 wherein the AED is configured to begin issuing operator instructions in response to the presence sensor detecting that the tray has been moved from the home position.

13. An AED as recited in claim 7 wherein the base defibrillator unit includes a controller configured to determine a presence of the electrode pad cartridge based on reading information from the security chip.

14. An AED as recited in claim 7 wherein the base defibrillator unit includes a controller configured to determine a type of electrode pad cartridge based on information stored on and read from the security chip.

15. An AED as recited in claim 7 wherein the base defibrillator unit includes a controller configured to identify, based on information read from the security chip, at least: (1) an adult electrode pad cartridge type when an adult electrode pad cartridge is attached to the base defibrillator unit; (2) a pediatric electrode pad cartridge type when a pediatric electrode pad cartridge is attached to the base defibrillator unit; and (3) a training electrode pad cartridge type when a training electrode pad cartridge is attached to the base defibrillator unit.

16. An AED as recited in claim 7 wherein the base defibrillator unit includes a controller configured to determine whether the electrode pads have been used based on information read from the security chip.

17. An AED as recited in claim 7 wherein the base defibrillator unit includes a controller configured to determine or read at least one of whether the electrode pads are expired, or an electrode pad expiration date based on information read from the security chip.

18. An AED as recited in claim 7 wherein the base defibrillator unit includes a controller configured to cause user instructions to be generated when the AED is activated, and wherein the instruction differ based on information read from the security chip.

19. An AED as recited in claim 7 wherein the electrode pads are attached to a webbing material that mechanically couples the electrode pads.

20. A method of activating an AED having one or more defibrillator electrode pad(s) associated therewith, the method comprising:
  while the AED is in a sleep or powered down mode, detecting that the defibrillator electrode pad(s) have been accessed; and
  activating the AED in response to the detection of the accessing of the defibrillator electrode pad(s).

21. A method as recited in claim 20 wherein the AED is configured to begin generating user instructions when the AED is activated.

22. A method of activating an AED having one or more defibrillator electrode pad(s) associated therewith, the method comprising:
  while the AED is in a sleep or powered down mode, detecting that the defibrillator electrode pad(s) have been accessed; and
  activating the AED in response to the detection of the accessing of the defibrillator electrode pad(s); and
  wherein when the AED is activated in response to the accessing of the defibrillator electrode pad(s), a controller that is part of the AED checks to determine a type of the defibrillator electrode pads that are associated with the AED;
  wherein the AED is configured to begin generating user instructions when the AED is activated; and
  the user instructions generated by the AED vary at least in part based on the determined type of defibrillator electrode pads.

23. An electrode pad cartridge comprising:
first and second defibrillation electrode pads;
a tray that carries the defibrillation electrode pads, the tray including a face plate, a base plate and drawer walls that extend outward from a first surface of the base plate to form a drawer box that receives the defibrillate electrode pads, each drawer wall including a seal surface on a free end of the drawer wall, wherein the tray includes a face plate that matches a contour of a defibrillator when the electrode pad cartridge is attached to the defibrillator; and
a foil secured to the wall seal surfaces, wherein the base plate, the drawer walls and the foil cooperate to help form a sealed drawer chamber in which the defibrillation electrode pads are stored; and
wherein the tray is configured to be pulled out in a drawer like manner relative to the defibrillator to facilitate accessing the sealed draw chamber.

24. An electrode pad cartridge as recited in claim 23 further comprising a pull tab that extends outward from the face plate, the pull tab being configured to be gripped by a user to pull the tray away from the defibrillator.

* * * * *

UNITED STATES PATENT AND TRADEMARK OFFICE
CERTIFICATE OF CORRECTION

| | | |
|---|---|---|
| PATENT NO. | : 12,194,305 B2 | Page 1 of 1 |
| APPLICATION NO. | : 17/725452 | |
| DATED | : January 14, 2025 | |
| INVENTOR(S) | : Andrews et al. | |

It is certified that error appears in the above-identified patent and that said Letters Patent is hereby corrected as shown below:

On the Title Page

1. In the Inventors Section – Item (72), please change "Gordon Mosely P. Andrews" to --Gordon Moseley P. Andrews--.

In the Specification

1. Column 1, Line 31, insert --.-- after "manner".

Signed and Sealed this
Twenty-seventh Day of May, 2025

Coke Morgan Stewart
*Acting Director of the United States Patent and Trademark Office*